United States Patent
Wang et al.

(10) Patent No.: US 9,386,957 B2
(45) Date of Patent: Jul. 12, 2016

(54) CT APPARATUS AND AN IMAGE PROCESSING METHOD USED BY THE SAME

(71) Applicant: GE MEDICAL SYSTEMS GLOBAL TECHNOLOGY COMPANY, LLC, Waukesha, WI (US)

(72) Inventors: Xue Li Wang, Beijing (CN); Zhenhua Xu, Beijing (CN); Jun Li, Chengdu (CN); Ximiao Cao, Beijing (CN); Bin Wang, ChengDu (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 206 days.

(21) Appl. No.: 14/167,124

(22) Filed: Jan. 29, 2014

(65) Prior Publication Data
US 2014/0211911 A1    Jul. 31, 2014

(30) Foreign Application Priority Data

Jan. 31, 2013    (CN) .......................... 2013 1 0037507

(51) Int. Cl.
A61B 6/00    (2006.01)
A61B 6/03    (2006.01)

(52) U.S. Cl.
CPC ............... *A61B 6/032* (2013.01); *A61B 6/4233* (2013.01); *A61B 6/5205* (2013.01); *A61B 6/5258* (2013.01); *A61B 6/583* (2013.01)

(58) Field of Classification Search
USPC .......................................................... 378/1, 4
See application file for complete search history.

(56) References Cited

U.S. PATENT DOCUMENTS

2008/0118023 A1*   5/2008   Besson ................... A61B 6/06
                                                                378/8

* cited by examiner

*Primary Examiner* — Nicole Ippolito
*Assistant Examiner* — Hanway Chang
(74) *Attorney, Agent, or Firm* — GE Global Patent Operation

(57) ABSTRACT

A method for automatically determining the best effective reconstruction gap, the method including scanning a phantom to collect image data of the phantom, using a plurality of different gap values to reconstruct image of the phantom respectively, based on the image data, thus obtaining a plurality of images respectively associated with different gap values, selecting the best image from the plurality of images, and automatically determining the gap value associated with the best image, and save it as the best effective reconstruction gap.

20 Claims, 8 Drawing Sheets

CT APPARATUS AND AN IMAGE PROCESSING METHOD USED BY THE SAME

TECHNICAL FIELD

In general, the present invention relates to computed tomography (CT) apparatus and image processing technologies, and in particular, the present invention relates to a method for automatically determining the best effective reconstruction gap, a method for removing a band artifact in a reconstructed image, a method for determining a band artifact parameter in a reconstructed image in a CT apparatus and the CT apparatus.

BACKGROUND ART

CT apparatuses have increasing application in the field of medical diagnosis and other fields. A CT apparatus mainly comprises an X-ray source, a collimator, a detector, a data acquisition system (DAS) and a data processing system. The currently used arc-shaped detectors are relatively expensive. A spiral volumetric CT apparatus (SVCT) is a novel CT that uses a flat detector technology, in which a detector consists of several (e.g., 5) flat modules, greatly reducing the cost of the detector.

However, since there are gaps (i.e. physical gaps) between the plurality of flat modules in the flat detector, a band artifact (or closed to be a ring artifact) is generated in a reconstructed image, which reduces the quality of the reconstructed image and severely affects accuracy of medical diagnosis made based on the image. Therefore, when the image is reconstructed, there is a need for removing the band artifact in the image caused by the gaps in the detector.

SUMMARY

One of technical problems to be solved by the present invention is to accurately and automatically determine the effective reconstruction gap to be considered when an image is reconstructed. Another technical problem to be solved by the present invention is to remove band artifact (or ring artifact) in a reconstructed image. A further technical problem to be solved by the present invention is to more accurately and objectively evaluate the severity of band artifact. A still further technical problem to be solved by the present invention is to provide a CT apparatus that overcomes the shortcomings of existing flat detector technologies.

According to a first aspect of the present invention, there is provided a method for automatically determining the best effective reconstruction gap in a CT apparatus, the CT apparatus comprising a detector consisting of a plurality of modules with physical gaps between said plurality of modules. The method comprises: scanning a phantom to collect image data of the phantom; using a plurality of different gap values to reconstruct image of the phantom respectively, based on the image data, thus obtaining a plurality of images respectively associated with different gap values; selecting the best image from the plurality of images; and automatically determining the gap value associated with the best image, and saving it as the best effective reconstruction gap.

In one embodiment of the present invention, selecting the best image from the plurality of images comprises manually selecting the best image by a user based on visual evaluation of band artifact in each of the images.

In one embodiment of the present invention, selecting the best image from the plurality of images comprises automatically selecting the best image by the CT apparatus based on calculation of band artifact parameter in each of the images.

In one embodiment of the present invention, the calculation of the band artifact parameter in each of the images comprises: estimating location and width of the band artifact in the image based on location and size of the physical gap and based on geometry of the CT apparatus; determining locations of a band artifact region of interest ROI_0, a first neighbor region of interest ROI_1 and a second neighbor region of interest ROI_2 based on the estimated location and width of the band artifact; averaging CT values of all pixels within the ROI_1 and the ROI_2 to obtain a background CT value; averaging CT values of all pixels within the ROI_0 to obtain a band artifact CT value; and calculating an absolute value of a difference between the background CT value and the band artifact CT value to obtain the band artifact parameter.

In one embodiment of the present invention, the calculation of the band artifact parameter in each of the images comprises: estimating location and width of the band artifact in the image based on location and size of the physical gap and based on geometry of the CT apparatus; determining locations of a band artifact region of interest ROI_0, a first neighbor region of interest ROI_1 and a second neighbor region of interest ROI_2 based on the estimated location and width of the band artifact; averaging CT values of all pixels within the ROI_1 and the ROI_2 to obtain a background CT value; sorting CT values of all pixels within the ROI_0 in descending order as $1^{st}$ pixel up to $N^{th}$ pixel, where N is the total number of pixels within the ROI_0; averaging the CT values of all pixels within the ROI_0 to obtain a ROI_0 CT value; comparing the background CT value and the ROI_0 CT value; determining that the band artifact parameter is equal to zero if the background CT value is equal to the ROI_0 CT value, and comparing the background CT value with the $1^{st}$ pixel and the $N^{th}$ pixel if the background CT value is not equal to the ROI_0 CT value; determining the ROI_0 CT value as a band artifact CT value if a condition that the background CT value is larger than the $1^{st}$ pixel or is less than the $N^{th}$ pixel is satisfied, or if said condition is not satisfied, sequentially fetching M pixels, starting from the $N^{th}$ pixel if the background CT value is less than the ROI_0 CT value, or sequentially fetching M pixel, starting from the $1^{st}$ pixel if the background CT value is larger than the ROI_0 CT value, until a mean value of CT values of the M pixels is equal to the background CT value, where $1 \leq M < N$, and then calculating a mean value of CT values of remaining (N−M) pixels within the ROI_0 as the band artifact CT value; and calculating an absolute value of a difference between the background CT value and the band artifact CT value to obtain the band artifact parameter.

In one embodiment of the present invention, the location of the physical gap is calculated based on serial numbers of detecting channels in the detector, while the size of the physical gap is actually measured.

In one embodiment of the present invention, the phantom is a water phantom.

In one embodiment of the present invention, the water phantom is small in size and is arranged in an off-centered manner.

In one embodiment of the present invention, the water phantom is small in size and is centrally arranged to cover only the physical gap of a center module in the detector.

In one embodiment of the present invention, the water phantom is large in size, and a large current of an X-ray source and a large slice thickness is employed when the water phantom is scanned.

In one embodiment of the present invention, the plurality of different gap values are entered manually by the user or set automatically by the system.

In one embodiment of the present invention, a standard kernel function and/or a sharp kernel function is employed during reconstructing the image of the phantom.

In one embodiment of the present invention, the sharp kernel function is a bone kernel function or an edge kernel function.

According to a second aspect of the present invention, there is provided a method for removing a band artifact in a reconstructed image in a CT apparatus, the method comprises: scanning an object to collect image data of the object; and reconstructing an image of the object based on the image data of the object by using the best effective reconstruction gap determined by said method according to the first aspect.

According to a third aspect of the present invention, there is provided a method for determining a band artifact parameter in a reconstructed image in a CT apparatus, comprising: estimating location and width of a band artifact in an image based on location and size of individual physical gaps between a plurality of modules in a detector of the CT apparatus; determining locations of a band artifact region of interest ROI_0, a first neighbor region of interest ROI_1 and a second neighbor region of interest ROI_2 based on the estimated location and width of the band artifact; averaging CT values of all pixels within the ROI_1 and the ROI_2 to obtain a background CT value; sorting CT values of all pixels within the ROI_0 in descending order as $1^{st}$ pixel up to $N^{th}$ pixel, where N is the total number of pixels within the ROI_0; averaging the CT values of all pixels within the ROI_0 to obtain a ROI_0 CT value; comparing the background CT value and the ROI_0 CT value; determining that the band artifact parameter is equal to zero if the background CT value is equal to the ROI_0 CT value, and comparing the background CT value with the $1^{st}$ pixel and the $N^{th}$ pixel if the background CT value is not equal to the ROI_0 CT value; determining the ROI_0 CT value as a band artifact CT value if a condition that the background CT value is larger than the $1^{st}$ pixel or is less than the $N^{th}$ pixel is satisfied, or if said condition is not satisfied, sequentially fetching M pixels, starting from the $N^{th}$ pixel if the background CT value is less than the ROI_0 CT value, or sequentially fetching M pixel, starting from the $1^{st}$ pixel if the background CT value is larger than the ROI_0 CT value, until a mean value of CT values of the M pixels is equal to the background CT value, where $1 \leq M < N$, and then calculating a mean value of CT values of remaining (N−M) pixels within the ROI_0 as the band artifact CT value; and calculating an absolute value of a difference between the background CT value and the band artifact CT value to obtain the band artifact parameter.

In one embodiment of the present invention, the location of the physical gap is calculated based on serial numbers of detecting channels in the detector, while the size of the physical gap is actually measured.

According to a fourth aspect of the invention, there is provided a CT apparatus, comprising: an X-ray source; a collimator; a detector consisting of a plurality of modules with physical gaps between said plurality of modules; and an image reconstructor for reconstructing an image of a scanned object by using the best effective reconstruction gap determined by said method according to the first aspect.

In one embodiment of the present invention, the plurality of modules in the detector is flat modules.

Embodiments of the present invention are capable of accurately and objectively evaluating image quality, automatically selecting the best effective reconstruction gap based on actual image quality; perfectly removing the artifact in an image; and enable a low cost flat detector to obtain a good image quality.

BRIEF DESCRIPTION OF DRAWINGS

Other objects, advantages and novel features of the present invention will become apparent from the following detailed description of the invention when considered in conjunction with the accompanying drawings, in which.

DETAILED DESCRIPTION

In the following, embodiments of the invention will be described in more detail with reference to some embodiments and to accompanying drawings. For purposes of illustration instead of limitation, some specific details are set forth, such as particular structures, systems and components, etc., in order to enable those skilled in the art to readily understand the present invention. However, it will be apparent to those skilled in the art that the present invention may be practiced in other embodiments without these specific details described herein. It will be appreciated by those skilled in the art that the solutions described herein may be implemented entirely or partly with hardware and/or software. The present invention is not limited to any specific combination of hardware and software.

Figure 1:
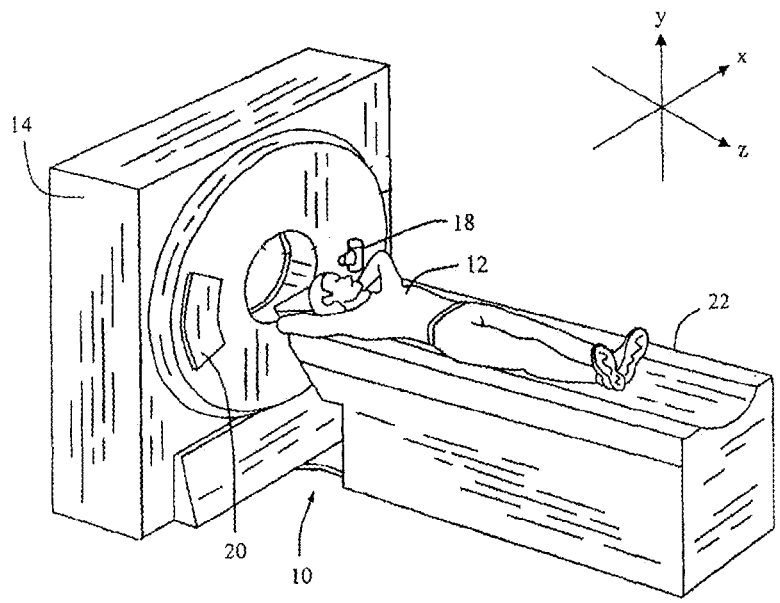
FIG. 1 schematically shows a simplified stereogram of a CT apparatus.

FIG. 1 schematically shows a simplified stereogram of an example CT apparatus. The CT apparatus 10 comprises a gantry 14; an X-ray source 18, a collimator (not shown) and an X-ray detector 20 that are mounted on the gantry; a table 22 for carrying an object to be scanned 12 (e.g., a patient or a phantom); and other components such as a data acquisition system (DAS) and a data processing system (not shown).

The X-ray detector 20 may be a traditional arc-shaped detector or a novel flat detector. Since manufacturing process of the traditional arc-shaped detectors can restrict the gaps between detector modules to be rather small, no significant band artifact will be introduced in a reconstructed image. The novel flat detector generally consists of a plurality (e.g., 5) of flat modules, and typically there are physical gaps between these modules, which will introduce significant band artifact in a reconstructed image. Therefore, the principles of the present invention will be illustrated below with respect to a flat detector. However, it should be noted that the principles of the present invention are applicable for any detector consisting of a plurality of modules with gaps between the modules. The present invention is independent of category, scanning mode or image reconstruction mode of CT apparatus.

Figure 2:
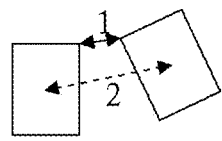
FIG. 2 schematically shows a physical gap and an effective reconstruction gap between adjacent modules in a detector.

FIG. 2 schematically shows a physical gap and an effective reconstruction gap between adjacent modules in a detector. The physical gap 1 is a distance between edges of two adjacent modules that can be actually measured. The effective reconstruction gap 2 is an effective gap that should be considered when an image is reconstructed. The effective reconstruction gap 2 depends on not only size of physical gap, but also many other factors such as centroid of scintillator, input X-ray spectrum, X-ray tube voltage, signal intensity, manufacturing error and so on. Therefore, it cannot be measured directly, and accurate calculation of the effective reconstruction gap 2 is difficult and complex.

Figure 3:
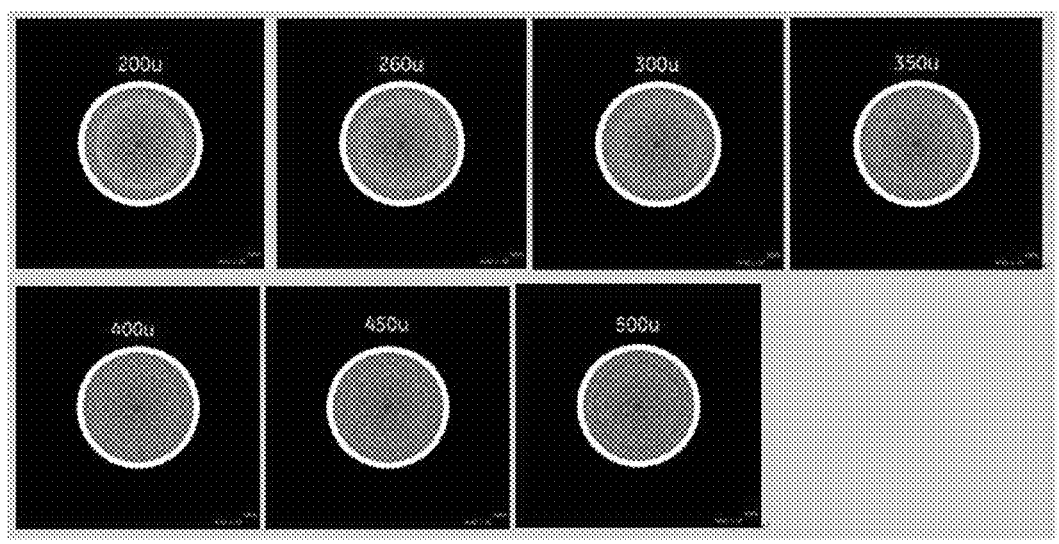
FIG. 3 shows a plurality of images of the same object reconstructed with different effective reconstruction gap values.

FIG. 3 shows a plurality of images of the same object reconstructed with different effective reconstruction gap values. As can be seen, the severity of the band artifact is closely associated with the gap values (200 µm, 260 µm, 300 µm, 350 µm, 400 µm, 450 µm, 500 µm) inputted when the image is reconstructed. Since none of the inputted gap values is the accurate (best) effective reconstruction gap, the band artifact appears in each image. The farther the deviation of the inputted gap value from the best effective reconstruction gap, the more significant the band artifact is.

Figure 4:
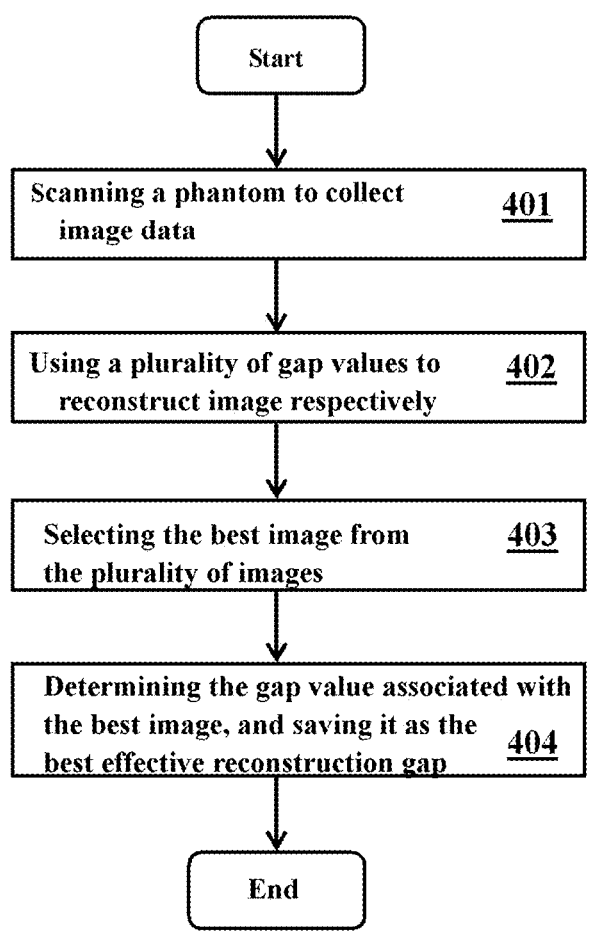
FIG. 4 schematically shows a method for automatically determining the best effective reconstruction gap according to one embodiment of the present invention.

FIG. 4 schematically shows a method for automatically determining the best effective reconstruction gap according to one embodiment of the present invention. The method 400 comprises: scanning a phantom to collect the image data of the phantom, 401; using a plurality of different gap values (manually entered by the user or automatically set by the system) to reconstruct the image of the phantom respectively, based on the image data, thus obtaining a plurality of images respectively associated with different gap values, 402; selecting the best image from the plurality of images, 403; and automatically determining the gap value associated with the best image, and saving it as the best effective reconstruction gap (e.g., saved in a profile for future use in scanning a patient), 404.

With regard to the phantom used as an object to be scanned, a water phantom that is closest to the density of a human body is often selected, but other phantoms may also be possible. When a phantom is selected, the main types of objects to be scanned by the CT apparatus in the future should be taken into consideration.

It should be noted that phantoms of different sizes may cover different physical gaps. For example, a phantom of larger size (e.g., a 42 pp phantom) may cover all gaps of a SVCT (with SFOV of 43 cm), but the obtained image may have larger noise. A plurality of band artifacts corresponding to each of the gaps and being entirely or partly overlapped with each other may appear in the reconstructed image. Therefore, to enhance the definition of the obtained image, in an embodiment, a large current of X-ray source and a large slice thickness are used when a larger phantom is scanned.

A phantom of smaller size (e.g., a 12.5 cm water phantom) may cover only the physical gap of the center module when it is located at the center (ISO), and may cover only the physical gaps of surrounding modules when it is off-center. However, the obtained image may have smaller noise, so that the band artifact may be visually clearer. Therefore, in an embodiment, a phantom of smaller size is selected for detecting the gap, by covering the first physical gap by the phantom and performing the method as shown in FIG. 4, determining the first best effective reconstruction gap corresponding to the first physical gap; then moving the location of the phantom to cover the second physical gap and again performing the method as shown in FIG. 4, determining the second best effective reconstruction gap corresponding to the second physical gap; and so on, until determining all of the best effective reconstruction gaps corresponding to all of the respective physical gaps, finally saving all of the best effective reconstruction gaps in the profile for later use.

In one embodiment of the present invention, when an image is reconstructed, a standard kernel function, which is commonly used clinically, but results in larger noise, may be used; or alternatively, a sharper kernel function such as a bone kernel function or an edge kernel function may be used, which results in lower noise, so that the band artifact is visually clearer. Of course, combination of the standard kernel function and the sharper kernel function may be also used.

In one embodiment of the present invention, since the detector modules take ISO as a central symmetry point, the band artifacts introduced by the left and right physical gaps are entirely overlapped with each other. If it is needed to distinguish each band artifact produced by each respective gap, a segment reconstruction method may be selected, for example, by using the data collected by one half of the detector (and using an asymmetry algorithm) to reconstruct an image, where only the artifact corresponding to a left or right gap appears.

Some alternative embodiments for scanning a phantom and reconstructing an image are briefly described above. The approach of selecting the best image will be described below.

In one embodiment of the present invention, the best image is selected manually by a user based on the visual evaluation of the band artifact in each image. In particular, the user selects an image with the least significant band artifact (i.e., the best image), while the gap value used in reconstructing this best image is recorded and saved in a profile by the CT apparatus based on selection result entered by the user.

In another embodiment of the present invention, the best image is selected automatically by the CT apparatus based on calculation of a band artifact parameter in each image. Various methods of calculating the band artifact parameter according to the principles of the present invention will be explained hereinafter with reference to FIGS. 5-8.

Figure 5:
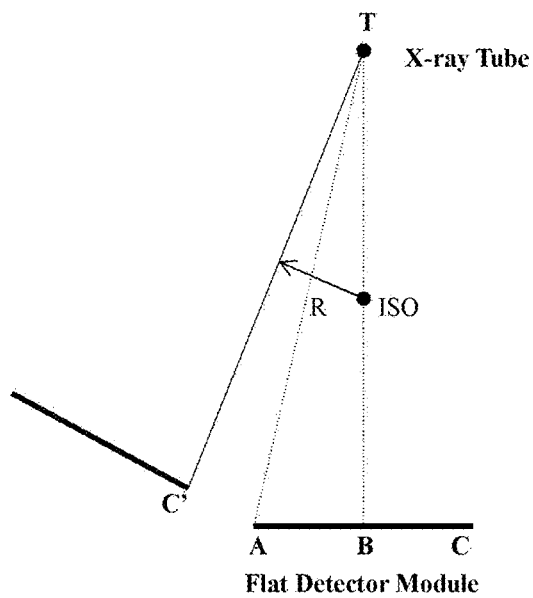
FIG. 5 schematically illustrates the relationship between the location of the physical gap of detector modules and the location of band artifact in a reconstructed image.

FIG. 5 schematically illustrates the relationship between the location of the physical gap of detector modules and the location of band artifact in a reconstructed image. As shown, T is the focus of the X-ray source, ISO is the rotational center; A and C are two ends of the center module, while B is the midpoint of the module; C' is the end of the adjacent module that is closer to the center module; R is the radius of the ring artifact for determining the location of the artifact. In the figure, the angle between TA and TB is referred to as half module angle $\beta$; the angle between TA and TC' is referred to as gap angle $\gamma$; and the angle between TB and TC' is referred to as $\alpha$. The following geometrical relations exist:

$R = \text{distance from } T \text{ to ISO} \times \sin\alpha$ $\alpha = \beta + \gamma$ $\beta = a\tan(AB \text{ length}/TB \text{ length})$, where the AB length=the total number of detecting channels in each module×single pixel size/2, $\gamma = a\sin(AC' \text{ length}/TA \text{ length})$, where AC' length is the size of the physical gap actually measured, TA length is the length from the X-ray tube to one end of the module, and $$TA \text{ length} = TB \text{ length}/\cos \beta.$$

With the above geometrical relations, it is possible to estimate the location and width of each band artifact in the image based on the location and size of each physical gap. The location of the physical gap is calculated based on the serial numbers of detecting channels in the detector, and the size of the physical gap is actually measured.

Figure 6:
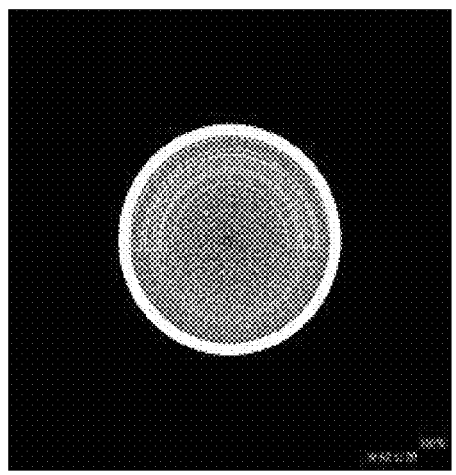
FIG. 6 shows the locations of a band artifact region of interest (a region drawn by yellow line, hereinafter referred to as "yellow region") and two neighbor regions of interest (regions drawn by blue lines, hereinafter referred to as "blue regions")

According to one embodiment of the present invention, the method for calculating the band artifact parameter comprises: estimating location and width of the band artifact in the image based on location and size of the physical gap and based on geometry of the CT apparatus; determining locations of a band artifact region of interest ROI_0, a first neighbor region of interest ROI_1 and a second neighbor region of interest ROI_2 (which correspond to a yellow region and two blue regions, as shown in FIG. 6) based on the estimated location and width of the band artifact; averaging CT values of all pixels within the ROI_1 and the ROI_2 to obtain a background CT value; averaging CT values of all pixels within the ROI_0 to obtain a band artifact CT value; and calculating an absolute value of a difference between the background CT value and the band artifact CT value to obtain the band artifact parameter.

This method is relatively simple. However, if the yellow region and two blue regions as shown in FIG. 6 are inaccurately drawn, the accuracy of the calculation result of the band artifact parameter will be adversely affected.

According to another embodiment of the present invention, a more robust method for calculating the band artifact parameter is proposed. The method further distinguishes between background pixels and artifact pixels within the yellow region as shown in FIG. 6, and thus more accurately identifies artifact pixels, so that the calculation of the band artifact parameter results in a more accurate and more objective value.

Figure 7:
FIG. 7 schematically shows the sorting of total N pixels within the band artifact region of interest.

The method comprises: estimating location and width of the band artifact in the image based on location and size of the physical gap and based on geometry of the CT apparatus; determining locations of a band artifact region of interest ROI_0, a first neighbor region of interest ROI_1 and a second neighbor region of interest ROI_2 (which correspond to a yellow region and two blue regions, as shown in FIG. 6) based on the estimated location and width of the band artifact; averaging CT values of all pixels within the ROI_1 and the ROI_2 to obtain a background CT value; sorting CT values of all pixels within the ROI_0 in descending order as $1^{st}$ pixel up to $N^{th}$ pixel, where N is the total number of pixels within the ROI_0 (as shown in FIG. 7), in which the sorting of CT values of pixels may use various sorting methods known in the art, such as bubble method, selection method, and the like; averaging the CT values of all pixels within the ROI_0 to obtain a ROI_0 CT value; comparing the background CT value and the ROI_0 CT value; determining that the band artifact parameter is equal to zero if the background CT value is equal to the ROI_0 CT value, and comparing the background CT value with the $1^{st}$ pixel and the $N^{th}$ pixel if the background CT value is not equal to the ROI_0 CT value; determining the ROI_0 CT value as a band artifact CT value if a condition that the background CT value is larger than the $1^{st}$ pixel or is less than the $N^{th}$ pixel is satisfied, or if said condition is not satisfied, sequentially fetching M pixels, starting from the $N^{th}$ pixel if the background CT value is less than the ROI_0 CT value (i.e., the background is darker and the band artifact is lighter), or sequentially fetching M pixel, starting from the $1^{st}$ pixel if the background CT value is larger than the ROI_0 CT value, until a mean value of CT values of the M pixels is equal to the background CT value, where $1 \leq M < N$, and then calculating a mean value of CT values of remaining (N−M) pixels within the ROI_0 as the band artifact CT value; and calculating an absolute value of a difference between the background CT value and the band artifact CT value to obtain the band artifact parameter.

Figure 8:
FIG. 8 schematically shows a process of sequentially fetching one or more pixels starting from the $N^{th}$ pixel.

It should be noted that, during the process of sequentially fetching M pixels starting from the $N^{th}$ pixel, M may start from 1 and gradually increment. Alternatively, M may start from a certain empirical value i between 1 and N, and gradually increment, i.e., M=i, i+1, i+2 . . . , until the mean value of CT values of the pixels being fetched is equal to the background CT value, as shown in FIG. 8.

In a special case, when the yellow region (i.e., the band artifact region of interest ROI_0) is initially drawn to be relatively small so as to only contain artifact pixels, the background CT value will always be larger than or less than all of the $1^{st}$ through the $N^{th}$ pixels (i.e., "the condition that the background CT value is larger than the $1^{st}$ pixel or less than the $N^{th}$ pixel is satisfied" described in the above method).

After the band artifact parameter is calculated by the method described above, the image quality can be evaluated quantitatively, so that the CT apparatus can automatically select the best image, and lock the best effective reconstruction gap associated with the best image.

It should be noted that, although the above method is to exclude background pixels from the yellow region (i.e., the band artifact region of interest ROI_0) as shown in FIG. 6, an alternative solution where artifact pixels are excluded from the blue regions (i.e., the first neighbor region of interest ROI_1 and the second neighbor region of interest ROI_2) may also be feasible. In such an alternative solution, typically, the blue region may initially be drawn to be relatively large so as to possibly cover some band artifact pixels. Then, the pixels within the blue region may be sorted in descending order by the aforesaid similar sorting method, while the mean value of the pixels within the yellow region may be taken as a reference value, and artifact pixels are gradually removed from the blue regions in a manner similar to that shown in FIG. 8. Of course, it is possible to take an outmost background region surrounding the blue region to calculate the background CT value as the reference value.

According to another embodiment of the present invention, there is provided a method for removing band artifact in a reconstructed image in a CT apparatus, comprising: scanning an object (e.g., a patient) to collect image data of the object; and using the best effective reconstruction gap determined by the above method to reconstruct the image of the object based on the image data of the object.

According to still another embodiment of the present invention, there is provided a CT apparatus, comprising: an X-ray source; a collimator; a detector consisting of a plurality of modules with physical gaps between them; an image reconstructor for reconstructing the image of the scanned object with the best effective reconstruction gap determined by the above method. In an embodiment, the plurality of modules is flat modules.

Figure 9:
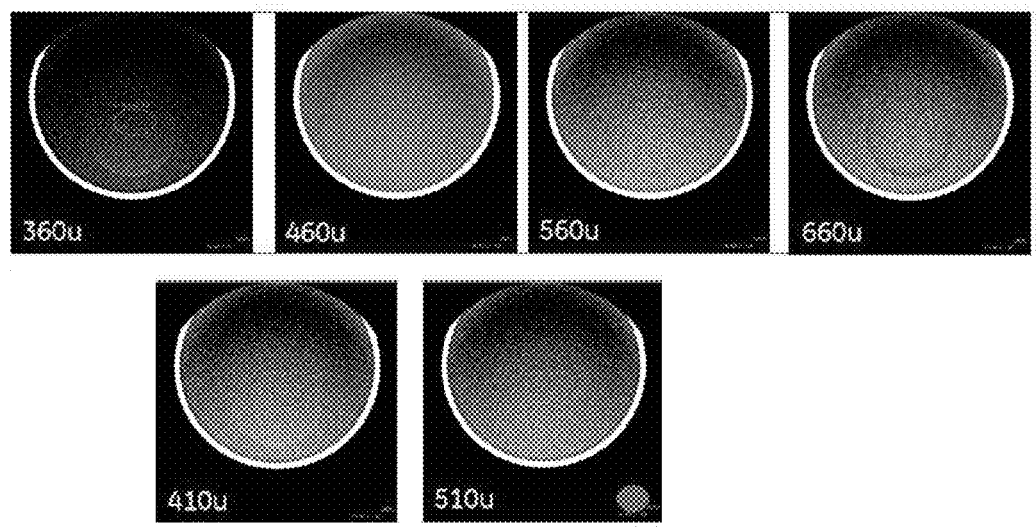
FIG. 9 shows six images of a water phantom reconstructed with six different gap values.

FIG. 9 shows six images of a water phantom reconstructed with six different gap values. The best image is selected by visual evaluation of image quality, and the gap value of 510 μm associated with the best image is determined as the best effective reconstruction gap.

Figure 10:
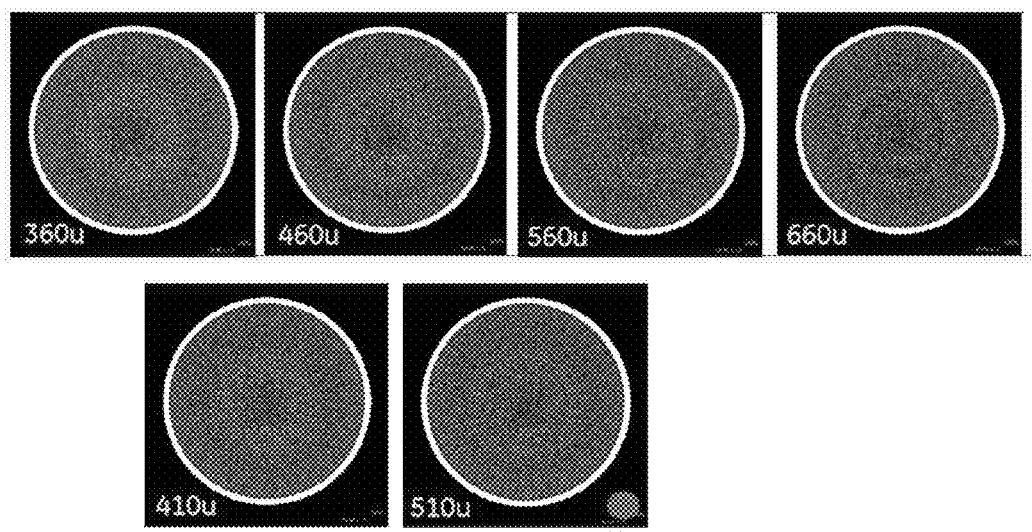
FIG. 10 shows the images of the center water phantom reconstructed with the aforesaid six different gap values.
Figure 11:
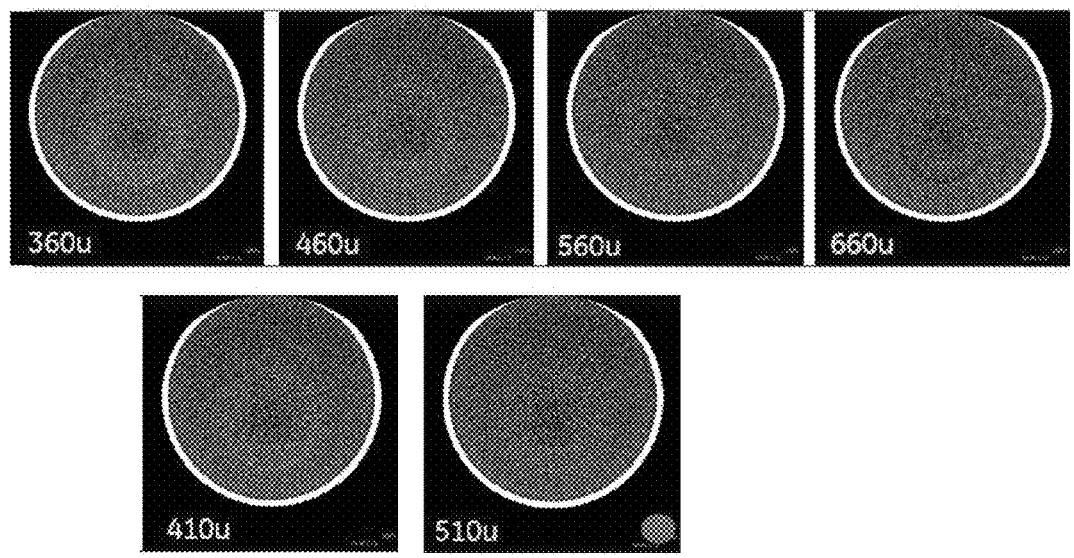
FIGS. 11, 12, 13, and 14 show the images of the off-center water phantom reconstructed with the aforesaid six different gap values.
Figure 12:
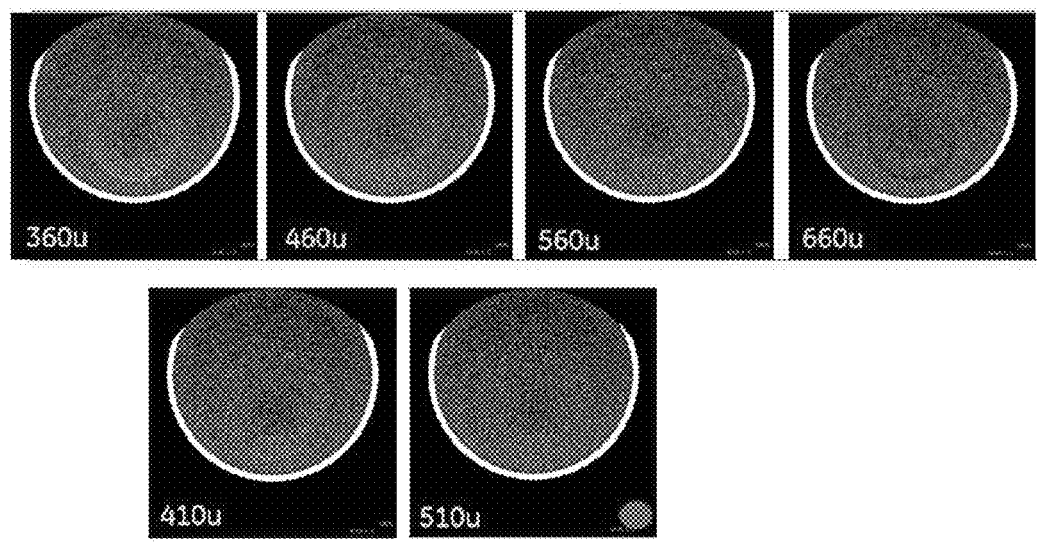
Figure 13:
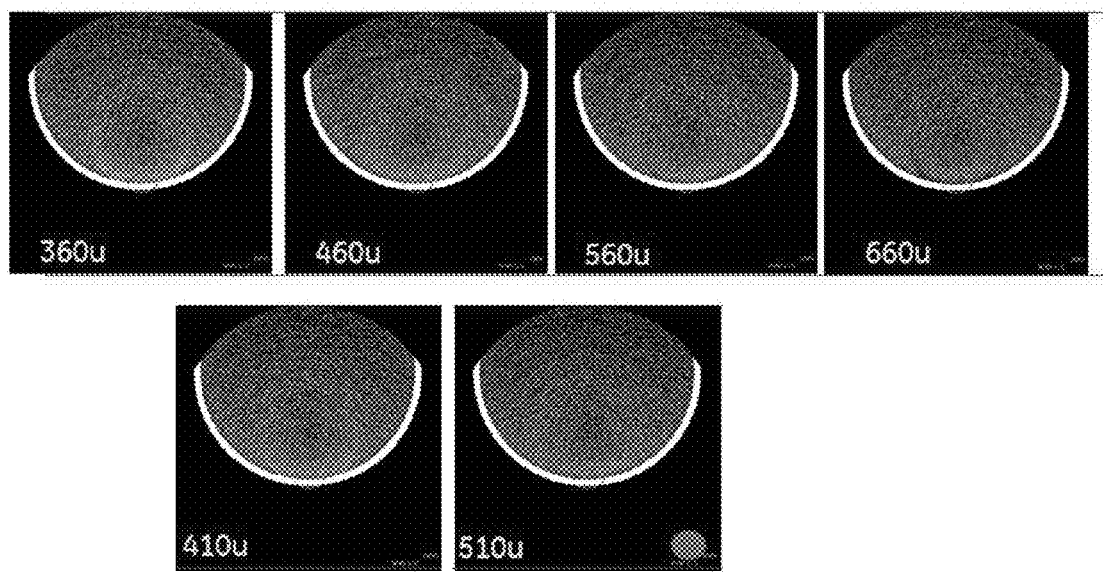
Figure 14:
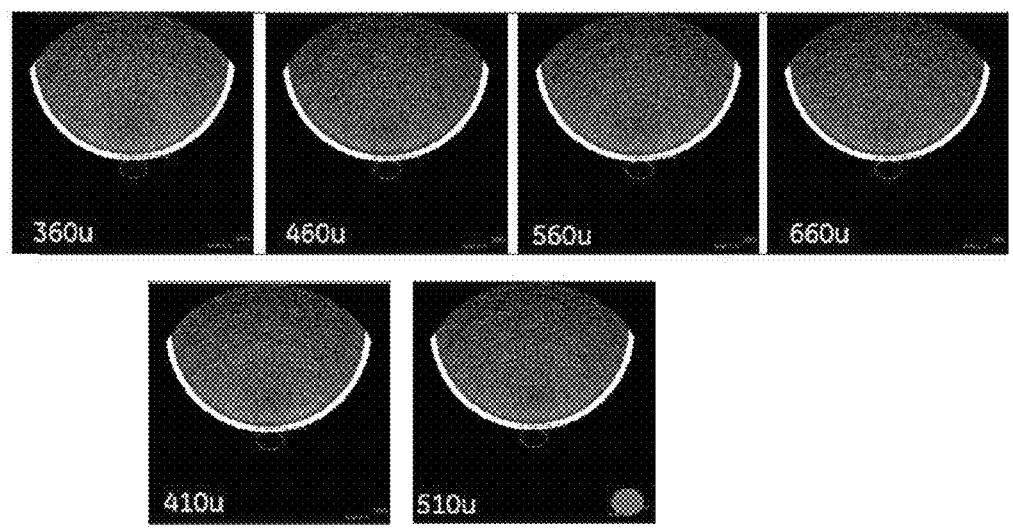

FIG. 10 shows the images of the center water phantom reconstructed with the aforesaid six different gap values. FIG. 11-14 show the images of the off-center water phantom reconstructed with the aforesaid six different gap values. As can be seen, the best effective reconstruction gap selected based on the reconstructed images of one phantom, when being used to reconstruct the images of other object (center water phantom and off-center water phantom), also properly removes the band artifact and results in the image with the best quality. Different phantoms have different sensitivities in terms of gap and visual image quality; however, the trends are the same, that is, the more inaccurate the effective reconstruction gap is, the more severe the band artifact in the reconstructed image is.

Additionally, since the image of the off-center phantom can be collected during the spectrum calibration, it is not necessary to add any special workflow.

Even though the effective reconstruction gap is related to the voltage kV (spectrum) of the X-ray source and the phantom, the method based on the actual image is accurate, because it is based on the phantom data and directed to every kV.

To sum up, embodiments of the present invention remove band artifacts to obtain a good image quality; and reducing the cost of a CT apparatus.

It should be noted that, in addition to the band artifact, other artifacts, such as center smear, scattered artifact, etc., might exist in the reconstructed image. Said other artifacts are not caused by inaccurate effective reconstruction gap, and may be removed in advance by using algorithms or methods known in the art, and then the method of the present invention may be used. How to remove other types of artifacts is not concerned by the present invention, and then will not be discussed any further.

The best effective reconstruction gap may be used to remove band artifact when the image is reconstructed, so that image quality is improved and the CT apparatus can employ a low cost flat detector, further reducing the cost of the CT apparatus.

The above mentioned and described embodiments are only given as examples and should not be construed to limit the present invention. Although specific terms may be employed herein, they are used in a generic and descriptive sense only and not for purposes of limitation. It is intended that the scope of the invention be defined only by the claims appended hereto, and their equivalents.

What is claimed is:

1. A method for automatically determining a best effective reconstruction gap in a CT apparatus, wherein the CT apparatus comprises a detector comprising a plurality of modules with physical gaps between the plurality of modules, the method comprising:
   scanning a phantom to collect image data of the phantom;
   obtaining a plurality of images by using a plurality of different gap values to reconstruct an image of the phantom, wherein each of the plurality of images is respectively associated with a gap value of the different gap values;
   estimating a location and a width of the band artifact in the image based on the location and the size of the physical gap, and based on the geometry of the CT apparatus;
   determining locations of a band artifact region of interest, a first neighbor region of interest, and a second neighbor region of interest based on the estimated location and the estimated width of the band artifact;
   averaging CT values of all pixels within the first neighboring region of interest and the second neighboring region of interest to obtain a background CT value;
   obtaining a band artifact CT value;
   calculating an absolute value of a difference between the background CT value and the band artifact CT value to obtain the band artifact parameter;
   selecting an image with the least significant band artifact as a best image;
   determining a gap value associated with the best image, and saving the determined gap value as the best effective reconstruction gap.

2. The method according to claim 1, wherein selecting the best image from the plurality of images comprises:
   selecting the best image by a user based on visual evaluation of a band artifact in each of the plurality of images.

3. The method according to claim 1, wherein selecting the best image from the plurality of images comprises:
   selecting the best image by the CT apparatus based on calculation of a band artifact parameter in each of the plurality of images.

4. The method according to claim 1, wherein obtaining a band artifact CT value
   comprises:
   averaging CT values of all pixels within the band artifact region of interest to obtain a band artifact CT value.

5. The method according to claim 1, wherein obtaining a band artifact CT value
   comprises:
   sorting CT values of all pixels within the band artifact of interest in descending order as $1^{st}$ pixel up to $N^{th}$ pixel, where N is the total number of pixels within the band artifact region of interest;
   averaging the CT values of all pixels within the band artifact region of interest to obtain a band artifact region of interest CT value;
   comparing the background CT value and the band artifact region of interest CT value;
   determining that the band artifact parameter is equal to zero if the background CT value is equal to the band artifact region of interest CT value, and comparing the background CT value with the $1^{st}$ pixel and the $N^{th}$ pixel if the background CT value is not equal to the band artifact region of interest CT value;
   determining the band artifact region of interest CT value as a band artifact CT value if a condition that the background CT value is larger than the $1^{st}$ pixel or is less than the $N^{th}$ pixel is satisfied, or if the condition is not satisfied, sequentially fetching M pixels, starting from the Nth pixel if the background CT value is less than the band artifact region of interest CT value, or sequentially fetching M pixel, starting from the $1^{st}$ pixel if the background CT value is larger than the band artifact region of interest CT value, until a mean value of CT values of the M pixels is equal to the background CT value, where $1 \leq M < N$, and
   calculating a mean value of CT values of remaining (N−M) pixels within the band artifact region of interest as the band artifact CT value.

6. The method according to claim 1, wherein the location of the physical gap is calculated based on serial numbers of detecting channels in the detector, while the size of the physical gap is actually measured.

7. The method according to claim 1, wherein the phantom is a water phantom.

8. The method according to claim 7, wherein the water phantom is small in size and is arranged in an off-centered manner.

9. The method according to claim 7, wherein the water phantom is small in size and is centrally arranged to cover only the physical gap of a center module in the detector.

10. The method according to claim 7, wherein the water phantom is large in size, and a large current of an X-ray source and a large slice thickness is employed when the water phantom is scanned.

11. The method according to claim 1, wherein the plurality of different gap values are entered manually by a user or set automatically by the CT apparatus.

12. The method according to claim 1, wherein a standard kernel function and/or a sharp kernel function is employed during reconstructing an image of the phantom.

13. The method according to claim 12, wherein the sharp kernel function is a bone kernel function or an edge kernel function.

14. A method for removing a band artifact in a reconstructed image in a CT apparatus, the method comprising:
   scanning an object to collect image data of an object;
   reconstructing an image of the object based on the image data of the object by using the best effective reconstruction gap determined by the method according to claim 1.

15. A method for determining a band artifact parameter in a reconstructed image in a CT apparatus, comprising:
   estimating location and width of a band artifact in an image based on location and size of individual physical gaps between a plurality of modules in a detector of the CT apparatus;
   determining locations of a band artifact region of interest, a first neighbor region of interest and a second neighbor region of interest based on the estimated location and width of the band artifact;
   averaging CT values of all pixels within the first neighbor region of interest and the second neighbor region of interest to obtain a background CT value;
   sorting CT values of all pixels within the band artifact region of interest in descending order as $1^{st}$ pixel up to $N^{th}$ pixel, where N is the total number of pixels within the band artifact region of interest;
   averaging the CT values of all pixels within the band artifact region of interest to obtain a band artifact region of interest CT value;
   comparing the background CT value and the band artifact region of interest CT value;
   determining that the band artifact parameter is equal to zero if the background CT value is equal to the band artifact region of interest CT value, and comparing the background CT value with the $1^{st}$ pixel and the $N^{th}$ pixel if the background CT value is not equal to the band artifact region of interest CT value;
   determining the band artifact region of interest CT value as a band artifact CT value if a condition that the background CT value is larger than the $1^{st}$ pixel or is less than the $N^{th}$ pixel is satisfied, or if the condition is not satisfied, sequentially fetching M pixels, starting from the $N^{th}$ pixel if the background CT value is less than the band artifact region of interest CT value, or sequentially fetching M pixel, starting from the $1^{st}$ pixel if the background CT value is larger than the band artifact region of interest CT value, until a mean value of CT values of the M pixels is equal to the background CT value, where $1 \leq M < N$, and
   calculating a mean value of CT values of remaining (N−M) pixels within the band artifact region of interest as the band artifact CT value; and
   calculating an absolute value of a difference between the background CT value and the band artifact CT value to obtain the band artifact parameter.

16. The method according to claim 15, wherein the location of the physical gap is calculated based on serial numbers of detecting channels in the detector, while the size of the physical gap is actually measured.

17. A CT apparatus, comprising:
   an X-ray source;
   a collimator;
   a detector comprising a plurality of modules with physical gaps between the plurality of modules;
   a processor configured to:
      determine a best effective reconstruction gap by processing a plurality of images, wherein each of the plurality of images is respectively associated with a gap value,
      estimate a location and a width of the band artifact in the image based on the location and the size of the physical gap, and based on the geometry of the CT apparatus;
      determine locations of a band artifact region of interest, a first neighbor region of interest, and a second neighbor region of interest based on the estimated location and the estimated width of the band artifact;
      average CT values of all pixels within the first neighboring region of interest and the second neighboring region of interest to obtain a background CT value;
   determine a band artifact CT value;
   calculate an absolute value of a difference between the background CT value and the band artifact CT value to obtain the band artifact parameter;
   selecting an image with the least significant band artifact as a best image; and
      determine the gap value associated with the best image as the best effective reconstruction gap; and
   an image reconstructor configured to reconstruct an image of a scanned object by using the best effective reconstruction gap.

18. The CT apparatus according to claim 17, wherein the plurality of modules in the detector are flat modules.

19. The CT apparatus according to claim 17, wherein obtaining a band artifact CT value comprises:
   averaging CT values of all pixels within the band artifact region of interest to obtain the band artifact CT value.

20. The CT apparatus according to claim 17, wherein obtaining a band artifact CT value comprises:
   sorting CT values of all pixels within the band artifact of interest in descending order as $1^{st}$ pixel up to $N^{th}$ pixel, where N is the total number of pixels within the band artifact region of interest;
   averaging the CT values of all pixels within the band artifact region of interest to obtain a band artifact region of interest CT value;
   comparing the background CT value and the band artifact region of interest CT value;
   determining that the band artifact parameter is equal to zero if the background CT value is equal to the band artifact region of interest CT value, and comparing the background CT value with the $1^{st}$ pixel and the $N^{th}$ pixel if the background CT value is not equal to the band artifact region of interest CT value;
   determining the band artifact region of interest CT value as a band artifact CT value if a condition that the background CT value is larger than the $1^{st}$ pixel or is less than the $N^{th}$ pixel is satisfied, or if the condition is not satisfied, sequentially fetching M pixels, starting from the $N^{th}$ pixel if the background CT value is less than the band artifact region of interest CT value, or sequentially fetching M pixel, starting from the $1^{st}$ pixel if the background CT value is larger than the band artifact region of interest CT value, until a mean value of CT values of the M pixels is equal to the background CT value, where $1 \leq M < N$, and calculating a mean value of CT values of remaining (N−M) pixels within the band artifact region of interest as the band artifact CT value.

\* \* \* \* \*